United States Patent [19]
Bokros et al.

[11] Patent Number: 5,137,532
[45] Date of Patent: Aug. 11, 1992

[54] PROSTHETIC HEART VALVE

[75] Inventors: Jack C. Bokros; Michael R. Emken, both of Austin; Axel D. Haubold, Liberty Hill; T. Scott Peters, Georgetown; Jonathan C. Stupka, Austin, all of Tex.

[73] Assignee: Onx, Inc., Austin, Tex.

[21] Appl. No.: 730,126

[22] Filed: Jul. 15, 1991

[51] Int. Cl.⁵ ............................................. A61F 2/24
[52] U.S. Cl. .................................... 623/2; 137/527; 251/212
[58] Field of Search .................... 623/2; 137/527; 251/212, 305

[56] References Cited

U.S. PATENT DOCUMENTS

| | | | |
|---|---|---|---|
| 3,118,468 | 1/1964 | Bochan | 623/2 X |
| 3,589,392 | 6/1971 | Meyer | 623/2 X |
| 3,689,942 | 9/1972 | Rapp | 623/2 |
| 3,744,060 | 7/1973 | Bellhouse et al. | 623/2 |
| 3,974,854 | 8/1976 | Kurpanek | 623/2 X |
| 4,078,268 | 3/1978 | Possis | 623/2 |
| 4,118,806 | 10/1978 | Porier et al. | 623/2 X |
| 4,178,638 | 12/1979 | Meyer | 623/2 |
| 4,308,624 | 1/1982 | Klawitter | 623/2 |
| 4,328,592 | 5/1982 | Klawitter | 623/2 |
| 4,597,767 | 7/1986 | Lenkei | 623/2 |
| 4,822,353 | 4/1989 | Bokros | 623/2 |
| 4,863,459 | 9/1989 | Olin | 623/2 |
| 4,863,467 | 9/1989 | Bokros | 623/2 |
| 5,041,131 | 8/1991 | Nagase | 623/2 X |

FOREIGN PATENT DOCUMENTS

| | | | |
|---|---|---|---|
| 1360724 | 12/1987 | U.S.S.R. | 623/2 |
| 1371700 | 2/1988 | U.S.S.R. | 623/2 |

Primary Examiner—Randall L. Green
Assistant Examiner—D. Willse
Attorney, Agent, or Firm—Fitch, Even, Tabin & Flannery

[57] ABSTRACT

Bi-leaflet heart valves have improved flow characteristics in their open position as a result of employing valve bodies of elongated axial dimension. By elongating the axial dimension of valve bodies which have straight, smooth interior wall surfaces oriented parallel to the centerline through the valve and to the flow path of blood, and by employing a pair of occluders which have major surfaces that are rectilinear and can assume an orientation that is substantially parallel to the centerline in the open position, a streamlining of blood flow occurs. The pivot arrangements avoid the use of acute angular surface orientations and cause the occluders, although aligned substantially parallel to blood flow in the open position, to promptly pivot toward the closed position upon reversal of blood flow. This streamlining substantially reduces turbulence and results in low head loss, both significant advantages in bi-leaflet heart valve performance.

4 Claims, 2 Drawing Sheets

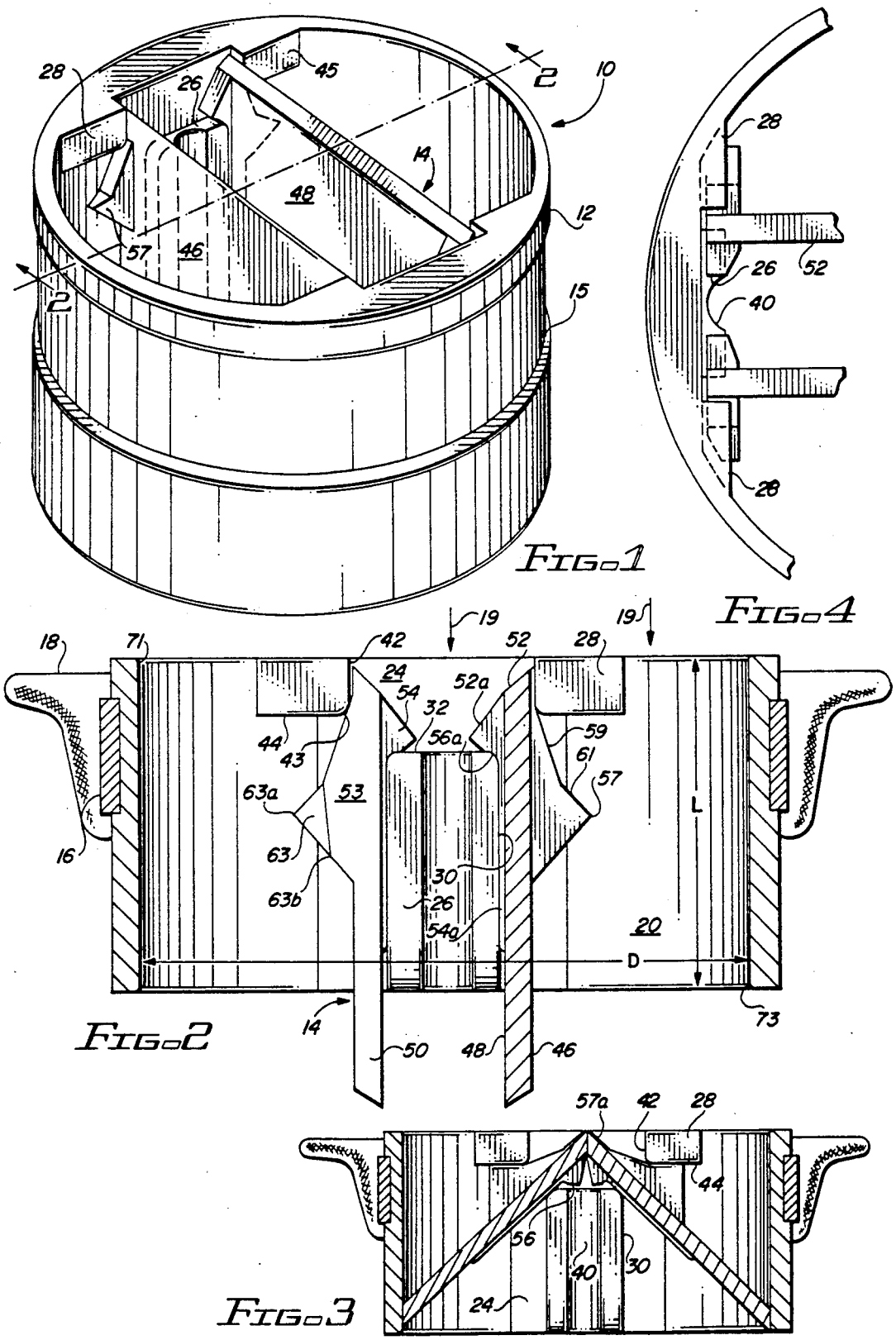

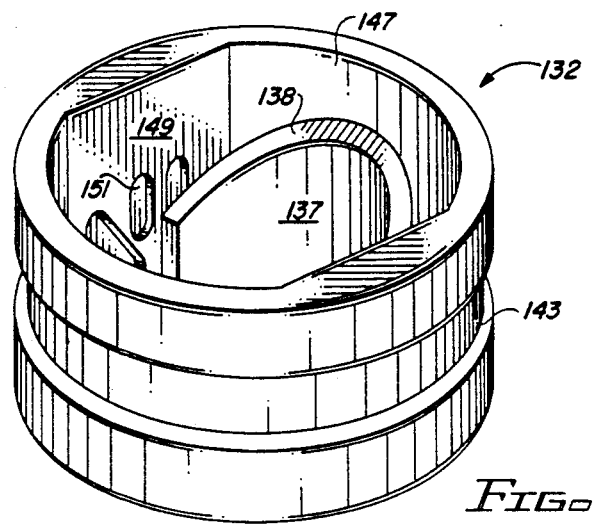
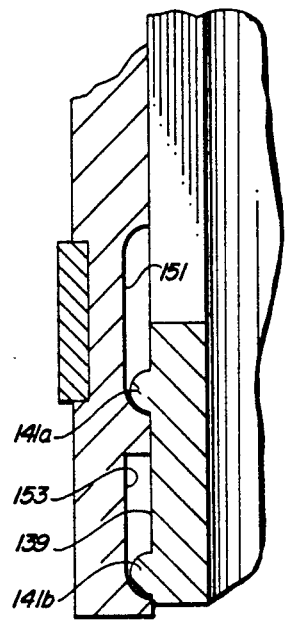
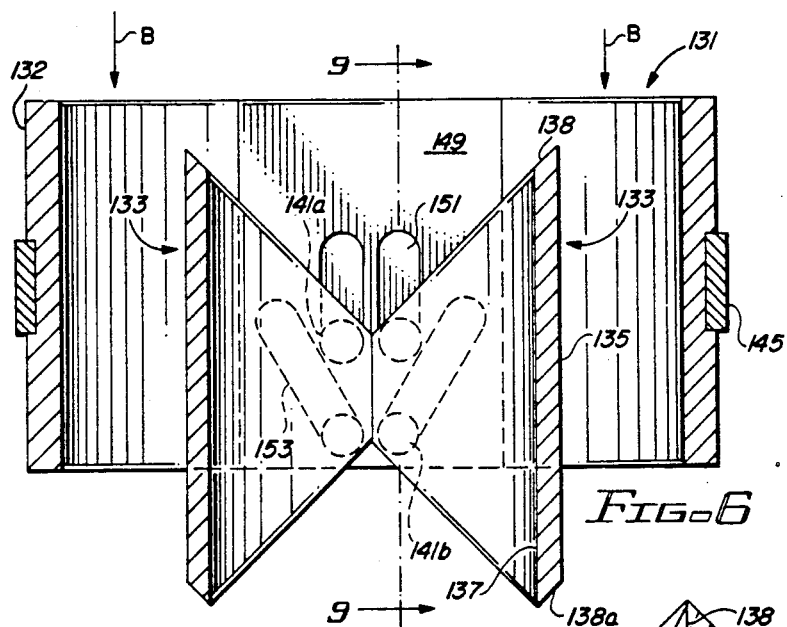
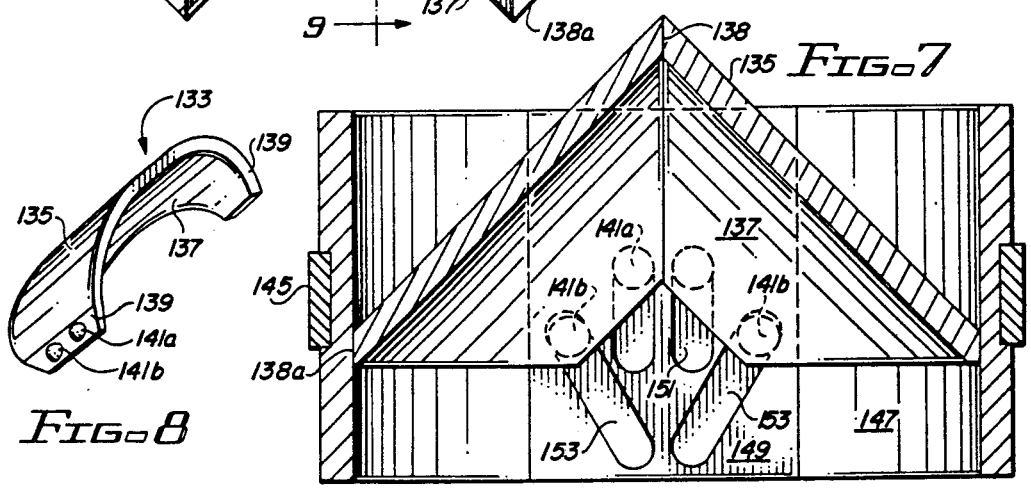

PROSTHETIC HEART VALVE

BACKGROUND OF THE INVENTION

The present invention pertains to heart valve prostheses and in particular, to prosthetic bi-leaflet heart valves wherein valve members generally pivot back and forth between open and closed positions.

DESCRIPTION OF THE PRIOR ART

Various types of heart valve prostheses have been developed which operate hemodynamically as a result of the pumping action of the heart. Such heart valves include valves having single occluders which pivot along an eccentric axis (or both pivot and translate), to open and close the blood flow passageway, such as those described in U.S. Pat. Nos. 3,546,711 and 4,725,275. They also include bi-leaflet heart valves, such as those described in U.S. Pat. Nos. 4,078,268, 4,159,543, 4,178,638, 4,308,624 and 4,535,484. The above-mentioned patents illustrate a number of different arrangements for pivotally connecting valve members (i.e. occluders) to valve bodies. U.S. Pat. No. 3,689,942 to R. K. Rapp shows a heart valve design having a generally square passageway closed by four pivoted occluders of generally triangular shape; it has a highly irregular sidewall which creates a lip extending inward that severely impedes blood flow.

In recent years, the bi-leaflet heart valve has generally become the mechanical valve of choice, and it is now felt that a prosthetic valve should provide an open position passageway which is large and which has good flow characteristics so that blood flows freely therethrough without adverse boundary layer separation and with a minimum of drag. Because of the general belief that the shorter the length, the less would be resistance to blood flow through the critical region of the valve, heart valve bodies, and particularly those for bi-leaflet valves, have been designed to be relatively short in axial length. For example, U.S. Pat. No. 3,926,215 issued in 1975 to Macleod, illustrates a mechanical check valve having a long tubular body with a frustoconical interior passageway wherein an occluder of generally aerofoil shape is pivoted. Although such a valve design is shown in FIG. 1, it is specifically pointed out in Column 2 of the patent that the illustrated valve having this tubular valve body is not applicable for use as a prosthetic heart valve by virtue of its proportions. Attention is then directed to FIG. 3 to show how such a valve body can be longitudinally or axially shortened to a proportion wherein the longitudinal or axial length of the valve body is a small fraction of the average diameter of the central passageway through the annular valve body. The foregoing has been indicative of the thinking of prosthetic heart valve designers who have advocated that the length of the valve body should be as short as possible so as to avoid creating too large a restriction to blood flow through the region of the valve. U.S. Pat. No. 4,276,658, shows the St. Jude Medical valve having a scalloped upstream or inflow end arrangement, wherein the pivot recesses are located, with the remainder of the valve body being substantially shorter in length.

Bi-leaflet heart valves have continued to be sought which have improved flow characteristics in the open position, avoid the likelihood of clotting, and retain reliability and responsiveness in operation.

SUMMARY OF THE INVENTION

The present invention provides bi-leaflet heart valves of improved flow characteristics having valve bodies with substantially smooth sidewalls and a length substantially longer than comparable prior art heart valves. When such valve bodies are coupled with leaflets that are generally pivoted or guided along their lateral edges and that are designed so that their outflow and inflow surfaces, in the open position, can be aligned substantially parallel to the longitudinal axis or centerline of the valve passageway, streamlined flow patterns are created past both opposite leaflet surfaces and through the valve body. This desirable streamlining effect is surprisingly achieved by having the bi-leaflet valve body proportioned so that its minimum axial length is greater than about 50% of the effective diameter of the opening which constitutes the central passageway. Preferably, this length is at least about 55%, and most preferably at least about 60% of the central passageway effective diameter, but usually not greater than about 150% thereof. The leaflets or occluders preferably have bodies of substantially uniform thickness throughout, except for those regions where structure responsible for the pivot arrangement may be located. Such occluders are then able to align themselves either substantially parallel to blood flow in the open position or to assume an equilibrium position a few degrees from precise parallel, and this feature, in combination with the elongated, smooth-walled valve body, results in streamlined flow and very low head loss through the valve. Preferably the axes about which occluders pivot are spaced radially from the longitudinal axis a distance not greater than about one-half the radius of the passageway so there is good flow past both surfaces.

BRIEF DESCRIPTION OF THE DRAWINGS

FIG. 1 is a perspective view of a bi-leaflet heart valve embodying various features of the present invention, shown in its open position;

FIG. 2 is an enlarged cross-sectional view of the heart valve taken along the line 2—2 of FIG. 1, also showing the valve with the leaflets in their open position, but with the lefthand leaflet shown in elevation instead of section;

FIG. 3 is a cross-sectional view, reduced in size, similar to FIG. 2 but showing both leaflets in cross section in their closed position;

FIG. 4 is a fragmentary plan view of the bi-leaflet heart valve shown in FIG. 2 with both leaflets shown in their open position, but without the metal stiffening ring and the sewing ring;

FIG. 5 is a perspective view of an alternative embodiment of a valve body for a bi-leaflet heart valve embodying various features of the present invention with only one of the two occluders installed;

FIG. 6 is a cross-sectional view, enlarged in size, of a heart valve including the valve body of FIG. 5 with both occluders installed and shown in the open position;

FIG. 7 is a cross-sectional view of the heart valve of FIG. 6 shown with the occluders in the closed position;

FIG. 8 is a perspective view of one of the occluders depicted in the heart valve of FIGS. 6 and 7; and FIG. 9 is an enlarged fragmentary, sectional view taken generally along the line 9—9 of FIG. 6.

DETAILED DESCRIPTION OF THE PREFERRED EMBODIMENTS

FIGS. 1-4 show a prosthetic heart valve embodying various features of the present invention. The heart valve 11 is of a bi-leaflet construction and has particularly improved flow characteristics with its valve members in the fully open position. The interior wall of the valve body 12 is smooth, parallel to blood flow and elongated in axial length, and this feature in combination with the ability of the occluders or valve members in the open position to assume parallel alignment, i.e. parallel to the centerline or longitudinal axis of the valve passageway, has been found to create a streamlined flow having extremely low loss in head pressure and minimal turbulence. Although other guide or pivot arrangements for the valve members can be employed, the illustrated arrangement is one that can be used and is described in detail in pending U.S. patent application Ser. No. 674,871, filed Mar. 25, 1991, the disclosure of which is incorporated herein by reference. Another useful pivot arrangement is shown in FIGS. 5-9.

Generally, the heart valve 10 includes a generally annular, elongated valve body 12, preferably formed of a pyrolytic carbon-coated graphite substrate, in which a pair of generally pivoting occluders or leaflets 14 are installed that open and close like a check valve to allow the flow of blood in a downstream direction, as indicated by the arrows 19 in FIG. 2, and prevent any substantial backflow in the upstream direction. The outer surface of the valve body preferably has a groove 15 which receives a metal stiffening ring 16 which in turn is designed to interconnect with and support a sewing ring 18 (see FIG. 2) of a conventional design as well-known in this art.

The blood flow passageway is defined by the interior sidewall or surface 20 of the valve body 12, and this surface is smooth and substantially parallel to the centerline. By substantially parallel is meant within about 3 degrees of true parallel. The passageway is generally that defined by a right circular cylindrical surface, which otherwise cylindrical surface is interrupted by a pair of diametrically opposed flat wall sections 24 that constitute the two oppositely facing regions where the pivot arrangements are located. As a result of the inclusion of these two flat wall interruptions 24 and the associated pivot projections, the effective diameter of the passageway, from its standpoint of providing a clear channel for blood flow, is reduced slightly as seen in FIG. 4, a fact which is discussed in more detail hereinafter. In the general region of each of these flat wall sections 24 is provided a central projection 26 and a pair of upstream flanking projections 28 which coact to define the generally pivotal or rotative movement of the leaflets 14 as they move from the fully open position to the closed position and vice versa.

As best seen in FIG. 1, these sets of projections 26, 28 extend generally perpendicularly from each flat wall section 24 of the interior sidewall. They are clean in outline, being preferably formed to have only generally right-angle or obtuse-angle orientations with adjacent surfaces 20, 24 of the interior passageway through the valve body 12; they are particularly devoid of any acute angle orientations of about 70° or less that would provide regions where there would be a high likelihood of the formation of blood clots. Although the protrusions 26, 28 provide minimal obstruction to the flow of blood through the passageway, even cleaner arrangements could be used, such as that shown in FIGS. 5 to 9, where each of the leaflets is controlled in its movement between open and closed positions by a pair of ears protruding from each lateral edge, which ears are received in pairs of elongated slots provided in the flat wall sections, as described hereinafter. Other suitable guide arrangements can also be used which permit the occluders or leaflets to assume a substantially parallel orientation in the full open orientation.

The central projection 26 has a pair of oppositely facing flat surfaces 30, each of which is parallel to the valve centerline, and an upstream surface 32 which is perpendicular thereto. The edges between these three surfaces can be faceted or rounded. The central portion of the projection is relieved by a concave groove 40 which minimizes the obstruction created by the presence of the projection 26 in the passageway. The projection extends to the downstream end of the valve body, and its downstream end is rounded. Alternatively, the projection can instead be tapered, if desired, for example, at a downstream angle of about 120 to 160 degrees to the flat sidewall section 24 to provide a smooth downstream transition surface.

Each of the flanking upstream projections 28 has a flat surface 42 which is also oriented parallel to the direction of blood flow, i.e. to the valve centerline, and each also has a downstream, generally perpendicular surface 44 and a flat interior wall surface 45 that extends to the curved interior sidewall of the valve body. The surfaces 42 and 44 intersect at what is termed downstream edge 43 of the projection, which may be faceted or slightly rounded. The interior surfaces 45 of the projections are parallel to the flat wall sections 24 of the valve body.

The leaflets 14 each have an upstream-facing or inflow surface 46 and an opposed downstream-facing or outflow surface 48, with reference to the leaflets when they are oriented in the closed position (see FIG. 3). Each leaflet thus has two essentially flat surfaces which constitute the major portion of its body, being only interrupted by lugs which protrude from the lateral edges and coact with the projections to guide the opening and closing movements of the leaflets. Accordingly, the major body portion of each leaflet is of uniform cross-sectional thickness, and both the inflow surface 46 and the outflow surface 48 can assume an alignment substantially parallel to the valve centerline when the leaflets are in the open position (FIG. 2).

Each of the leaflets 14 has a major arcuate edge surface 50, which is located at its downstream edge, and a minor mating edge surface 52 which is located at the opposite upstream edge, with respect to the leaflet in its open position. The arcuate edge surface 50 is configured to abut and seat against the smooth cylindrical sidewall 20 of the valve body in the closed position, whereas the minor mating edge surface 52 is of a configuration so as to mate with the corresponding mating edge surface of the other of the pair of leaflets. Accordingly, this minor surface 52 is flat and oriented at an angle such that the two mating edge surfaces abut while extending diametrically across the valve passageway in the closed position, as is well known in the art of bi-leaflet valves.

The leaflets 14 each include a pair of opposed lateral edge surfaces 53 which lie between the major arcuate surface and the minor mating surface and which are preferably flat. The leaflets 14 are proportioned so as to provide minimal clearance between the flat wall sections 24 of the valve body and the opposed intermediate lateral edge surfaces 53 so as to enable the leaflets to pivot, with these lateral edge surfaces 53 moving adjacent to the flat wall sections 24 and with one of them usually serving as a bearing surface. The projections 26 and 28 are located so that the surfaces which guide the leaflets in their sliding-pivotal movement are located within a distance from the centerline plane not greater than about one-half the radius whereby, in the open position the leaflets are spaced from the centerline plane a distance not greater than one-half the radius. By "centerline plane" is meant the plane perpendicular to the flat wall sections 24 which contains the longitudinal axis or centerline of the valve passageway.

Extending from the outflow surface 48 of each leaflet along its lateral edge is an integral first or opening lug 54, each leaflet having a pair of these lugs 54 which extend toward the centerline plane of the valve in the open position. These lugs have upstream surfaces 52a that are beveled, i.e. slightly angularly offset from the plane of the minor edge surface 52; this offset prevents interference with each other during movement toward the closed position (see FIG. 3). These lugs 54 have downstream surfaces 56 oriented to lie in juxtaposition with the transverse surface 32 of the central projection in the closed position, and these downstream surfaces are preferably oriented at an angle of between about 30 and about 45 degrees to the centerline plane in the open position. The downstream surfaces 56 are also preferably formed with a recess 56a which accommodates the rounded edge of the projection 26 when in the open position (see FIG. 2); this engagement with the projection 26 prevents the leaflet from escaping downstream.

Second or closing lugs 57 are also formed in each side section of each leaflet, as an integral part thereof, which protrude from the inflow surface 46 of each leaflet along each lateral edge. These second lugs 57 have a front camming surface 59 which is arranged so as to lie at a desired acute angle to the plane of the flat surface of the major body portion of the leaflet. These closing lugs 57, sometimes referred to as the inflow surface lugs, have their front camming surfaces 59 oriented at an angle between about 5 degrees and about 35 degrees to the centerline plane in the open position; they also have a rear angular surface 61 which is oriented so as to lie generally in juxtaposition with the transverse surface 44 of the upstream projections 28 when the leaflets are in the closed position.

The radially outer lateral surfaces of the lugs 57 are chamfered near their upper ends to provide a small generally triangular surface 63 on each lug that generally provides clearance when the lug 57 rotates in the region beyond the flat wall 24 of the valve body. Moreover, the chamfer is precisely located so as to create bearing ears 63a and b which can engage the curved sidewall of the valve body along axially oriented rub lines during intermediate portions of the closing movement of the leaflets; these bearing ears assist in guiding the rotation of the leaflets, particularly after each leaflet has lost sliding contact with the downstream projection 26 as a result of its being displaced upstream by the reverse flow of blood. The sizing of the leaflets 14 is such that simultaneous contact between ears along both opposite lateral sides and the interior cylindrical valve body sidewall 20 does not occur.

The leaflets 14 are installed in the valve body by squeezing the body at diametrically opposed locations so as to cause the flat wall sections 24 to separate further from each other and allow the leaflets to be fitted into the passageway of the valve body in their operative positions. The side sections which carry the respective lugs are thus received between each central projection 26 and one of the flanking upstream projections 28. When squeezing force is removed, the valve body returns to its original circular configuration, leaving the desired minimal clearance, with the leaflets being slidably-pivotally mounted for travel between their closed and open positions. The metal stabilizing ring 16 can be appropriately installed, as by shrink-fitting, following the installation of the leaflets; however, it may be preferred to first install the metal stabilizing ring which can improve the structural properties of a pyrocarbon valve body, the preferred material of construction. The illustrated design allows the leaflets to assume a precisely parallel orientation in the open position while, assuming this is the "low energy" or equilibrium position, still assuring that closing movement of the leaflets begin immediately as flow reversal occurs.

The fully open leaflet position is shown in FIG. 2 wherein the recess 56a of the first lug is in contact with the rounded edge between the surfaces 30, 32 of the central projection and wherein the flat outflow surface 48 of the leaflet lies in juxtaposition with one of the flanking surfaces 30 of the central projection so that the leaflets are oriented precisely parallel to the centerline. Front extensions 57a on the closing lugs 57 also lie in juxtaposition with the surfaces 42 of the upstream projections 28. As a result, the leaflets create minimal obstruction to the downstream flow of blood, and their locations create regions of very substantial blood flow adjacent both surfaces of each leaflet as a result of the open leaflet being located a distance from the centerline plane not greater than about one-half the radius.

When blood flow reverses as a result of the contraction of the heart, the backflow of blood creates a drag on the surfaces of the leaflets, displacing each leaflet upwardly so that the camming surface 59 of each closing lug immediately engages the curved edge of each upstream projection 28, causing the leaflet to immediately begin to rotate as it continues to slide upward. This prompt rotation continues, exposing the outflow surface 48 of the leaflet to more and more of the full force of the backflowing stream of blood, and thereby amplifying the rotative force vector being applied against each leaflet. Rotation and translation continues until the leaflets reach the closed position shown in FIG. 3 where they are preferably oriented with their flat main body sections at an angle of between about 30 and about 45 degrees to the centerline plane and with the surfaces 56 of the lugs 54 spaced just slightly above, but in juxtaposition with, the upstream transverse surfaces 32 of the central projection 26.

As soon as the next cycle occurs so that there is again a flow of blood in the normal downstream direction through the valve, the force of blood on the inflow surfaces 46 causes immediate displacement of the leaflets slightly downward until the surface 56 of the opening lugs contacts the transverse surface 32 of the center projection. This causes pivoting of the leaflets toward the open position to quickly occur, with such pivoting being primarily guided by the engagement between the surfaces 56 and 56a of the opening lugs with the center projection 26. Rotation continues until the open position is reached, wherein the leaflet or a thin extension 54a of the lug 54 is in contact with the surface 30, and the leaflets can assume this precise parallel position with respect to the valve centerline or, depending upon the blood flow pattern in the heart at that instant, can assume a low energy or equilibrium position that may be a few degrees short of parallel. In the open position, the rounded upstream edges of the projection 26 interengage with and are received within the recesses 56a, and the front extensions 57a of the second lugs 57 lie adjacent or engage the surfaces 42 of the projections 28.

It has been found that by proportioning the valve body so that it is elongated in length with respect to the diameter of the central passageway, unexpected advantages occur in a prosthetic heart valve where the occluders are aligned substantially parallel to the flow of blood through the valve in the open position and the sidewall of the valve body is smooth and substantially parallel to the centerline. The valve body sidewall that defines the blood flow passageway should be free of surfaces oriented at an acute angle of about 70° or less to each other also free of any generally upstream oriented surfaces. Preferably, there are no surfaces oriented so that they could potentially create turbulence and/or provide regions where there would be a high likelihood of clotting. It was found that, by appropriately elongating the valve body so that the minimum axial length at any location about the periphery of the interior passageway meets the aforementioned criterion, the relatively elongated length of the valve body causes a streamlined blood flow to be created which results in unexpectedly low head loss across the valve and minimal turbulence. Another significant advantage which arises from this construction is the ability to design the valve so that the amount of angular rotation through which the leaflets travel can be reduced, if desired, by having the leaflets reach the closed position oriented at a downstream angle to the centerline of as low as about 35°, usually between about 35° and 45°. Generally the lower the amount of angular rotation is, the more quickly the valve will close, and the less be the volume of blood which regurgitates.

More specifically, the valve body 12 has a very slightly rounded entrance edge 71 and a very slightly rounded exit edge 73; accordingly, the length L of the valve body 12 in the axial direction is measured as shown on FIG. 2 and covers the entire straightline section of the interior sidewall. The illustrated valve body 12 is of uniform axial length about its periphery; however, if the valve body were scalloped or otherwise shaped to have a varying axial length at certain locations, it would be the minimum axial length which is considered to be important because of the effect that such variance in length about the periphery of the passageway has on the streamlining of the blood flow pattern.

If the valve body 12 had an interior passageway which was that of a total right circular cylinder, then the effective diameter of the passageway would be the actual interior diameter D of the valve body opening. However, as indicated above and best seen in FIG. 4, the valve body 12 has a pair of diametrically opposed flat wall sections 24 and is also narrowed further in these locations by the presence of the projections 26 and 28. In this instance, an appropriate value, which is referred to as the effective diameter D', is calculated that is equal to the diameter of a circle having the same cross-sectional area of the open region of the valve body central passageway. Calculations show that flat sections 24 of the proportions seen in FIGS. 1 and 4 only reduce the cross-sectional area through the valve body by about 4%; accordingly for valve bodies of such generally circular cross section, the axial minimum length is preferably equal to at least about one-half of the interior diameter. The presence of the projections 26, 28, which extend inward from the flats 24, further reduce the open region so that it is only equal to about 93% of the complete circle. Accordingly, for a prosthetic heart valve 10 having a nominal interior diameter of 0.935 inch, the effective diameter (reduced for the presence of the flats and the projections) would be about 0.903 inch, about 96.5%. Preferably, the valve body is constructed so that it has an effective diameter D' equal to at least about 95% of the nominal interior diameter D, i.e. the diameter measured parallel to the two flat wall sections.

It has been found that such improved flow characteristics through the open valve are achieved in a valve body having the aforementioned characteristics, when the occluders are substantially parallel to blood flow in the open position and when the ratio of the minimum axial length L to the effective diameter D' is at least 0.5:1 and preferably at least about 0.55:1 and not greater than about 1.5:1. Most preferably, the ratio L to D' should be at least about 0.6:1 to achieve particularly improved streamlining and minimum head loss; moreover, to avoid overly long axial length that may render implantation more difficult, it may be more preferable that the L to D' ratio is between about 0.6:1 and about 1.2:1. In some instances, it is felt most preferable that the L to D' ratio is between about 0.6:1 and about 1:1. By designing the valve body to fall within these criteria and to have an interior wall surface of the aforementioned characteristics, and by employing a pair of occluders that are substantially uniform in thickness and have inflow and outflow surfaces that can be aligned substantially parallel to the centerline in the open position and are mounted so there is substantial blood flow past both the outflow and inflow occluder surfaces, unexpected streamlining of the flow patterns through the valve passageway is achieved that provides important performance advantages including a substantial reduction in head loss and turbulence compared, for example, to commercially available bi-leaflet valves having an L to D' ratio of about 0.25:1.

Shown in FIGS. 5–9 is an alternative embodiment of a bi-leaflet heart valve 131 which also incorporates an elongated valve body construction 132; it employs a pair of curved leaflets 133 and a different type of pivot mechanism, but one which also allows the leaflets to assume an orientation in the open position with their rectilinear surfaces parallel to the centerline of the valve and thus substantially parallel to the flow of blood through the valve. The heart valve 131 has a pair of leaflets 133, each of which has a convex inflow surface 135 and a concave outflow surface 137, these rectilinear surfaces form the main body portion of the leaflet which has a sidewall of uniform thickness except for the two regions along the lateral edges where there is a slight thickening to create a pair of flat surface sections 139 from which a pair of ears or bosses 141 protrude, which coact to define the pivoting-sliding motion of the leaflets. In essence, therefore, each leaflet 133 is generally a section of a tube or hollow cylinder of elliptical or oval cross-section, as perhaps best seen in FIG. 8, and has a flat upstream mating edge 138 and a downstream arcuate edge 138a. As a result of this construction, as shown in FIG. 6, the valve 131 in its open position has an enlarged central flow channel, compared to the valve 10 where two flat leaflets are employed.

The valve body 132 is again elongated in axial length, having an axial dimension equal to about 60 percent of the effective internal diameter of the valve body. The annular valve body 132 is essentially that of a hollow right circular cylinder again having a groove 143 in its exterior surface designed to accommodate a metal stiffening ring 145; the stiffening ring 145, shown installed in FIGS. 6, 7 and 9, as discussed hereinbefore is used for the attachment of a standard sewing ring (not shown) to the valve as well known in this art. An otherwise cylindrical interior sidewall surface 147 of the valve body 132 is interrupted by a pair of diametrically opposed flat wall sections 149, all of which are smooth and parallel to the centerline through the valve body. Two pairs of relatively shallow slots 151, 153 in each of the flat wall sections receive the ears 141 on the leaflets and coact therewith to define the movement of the leaflets between the open and closed positions. As best seen, perhaps, in FIG. 9, the ears 141 which project from the side sections 139 of the leaflets are spheroidal in shape, being illustrated as hemispheres of a curvature that essentially matches the radius of curvature of the shallow slots 151 and 153; the slots have a just slightly greater radius of curvature to assure there will be smooth movement of the ears within the slots.

In the open position illustrated in FIG. 6, the leaflets 133 are located at the downstream end of both slots 151, 153, with normal blood flow through the valve being in the downstream direction of the arrows B. Although the leaflets are curved in profile, their main body surfaces are rectilinear, i.e. made up of a locus of straight lines which extend parallel to the centerline of the valve in the open position, and provide minimal resistance to blood flow in the downstream direction. As soon as blood flow reverses, the leaflets 133 are displaced upstream in translational movement guided by the coaction of the spherical ears 141 in the pairs of slots 151, 153.

As can be seen in FIGS. 6 and 7, the upstream slots 151 are straight and parallel to the centerline of the valve passageway. The downstream slots are also straight, but are oriented at an upstream angle of about 35° to the orientation of the upstream slots and also to the valve centerline plane, the orientation being such that the slots 151, 153 diverge from each other in an upstream direction. Therefore, as upstream displacement of the leaflets occurs, although the ears 141a can move directly upstream in the upstream slots, the simultaneous movement of the ears 141b in the oblique slots 153 causes pivoting of the leaflets to immediately begin because the ears in the slots 153 are being forced away from the centerline plane while the sidewalls of the slots 151 restrain the ears 141a therein from any movement but that in an axial direction. As can be seen from FIGS. 6 and 7, the length of the oblique slots 153 is longer than the slots 151 which are parallel to the centerline. Accordingly, the ears 141b travel farther than do the ears 141a as the upstream movement continues; this movement is in the form of a pivoting motion about the ears 141a, which ears themselves are also moving upstream in the valve body as this pivoting of the leaflet is occurring. About the time the ears 141a reach the upstream ends of the slots 151, the flat surfaces of the mating edges 138 of the leaflets abut each other, and the arcuate downstream edges 138a of the leaflets abut the right circular cylindrical interior sidewall 147 of the valve body to provide a seal about the periphery of the leaflets in this region. The ears 141b preferably halt just short of the upstream ends of the slots 153. As in the case of the other leaflets hereinbefore described, the proportioning is such that the flat side sections 139 of the leaflets are located in essentially sliding contact with the flat interior wall sections 149 of the valve body, thus providing both bearing surfaces and seals in these regions.

When normal blood flow resumes, downward displacement of the leaflets 132 causes such sliding-pivoting action to be carried out in the reverse direction, again guided by the sliding engagement of the ears 141b along the downstream edges of the oblique slots 153 and of the ears 141a in the parallel slots 151. This pivoting action continues as the leaflets 133 move downward within the valve body 132 from the closed position depicted in FIG. 7 to the open position depicted in FIG. 6 wherein both ears are at the bottoms of their respective slots and wherein alignment of the major surfaces of each leaflet body is precisely parallel to the centerline. Because the surfaces which define the main body portion of each leaflet are oriented substantially parallel to the direction of blood flow in the open position, the leaflets 133 present minimal resistance to blood flow and, in combination with the elongated valve body, create the straightened, streamlined flow through the valve with a substantial reduction in turbulence and head loss as compared to comparable valves.

In summary, the invention provides bi-leaflet heart valves having unexpected advantages that result from the creation of streamlined flow through the valve because of the elongated parallel, smooth interior sidewalls of the valve body and the orientation of the leaflets parallel to blood flow through the passageway. The consequence of this streamlined flow is substantially reduced turbulence (which is presently being considered to be of more and more importance in the design of bi-leaflet prosthetic heart valves) and in a very low pressure drop or head loss across the valve itself, which is particularly advantageous in reducing the amount of work the heart must perform.

Typical peak flow through an aortic prosthetic valve during a cardiac cycle is between about 15 and about 50 liters per minute (lpm) depending upon the valve size, the heart rate, and the stroke volume or cardiac output. For example, a 23 mm diameter valve at 72 beats per minute (bpm) and a 6 lpm cardiac output would have a peak flow of about 30 lpm, whereas, under the same conditions, a smaller 19 mm valve may have a peak flow rate as high as about 40 lpm, which is of course representative of the higher velocity of the blood passing through the smaller valve opening. Because aortic valves are smaller than mitral valves, the blood flow (i.e., cardiac output) must traverse the valve at a higher velocity; thus, pressure drop improvement is of particular importance in aortic valves which are only open about one-half the time that mitral valves are open as a part of the normal cardiac cycle.

Furthermore, while the foregoing reference was to the peak flow rate through an aortic valve, it is important to realize that flow through aortic valves remains relatively high throughout the major portion of the entire pumping cycle. For example, because the forward or pumping part of the flow through an aortic valve constitutes only about 35 percent of the time of one overall cycle, an aortic valve of about 23 millimeters in diameter, in a heart operating at 72 beats per minute and an output of 6 lpm, would have a mean flow rate of about 19 lpm along with a peak flow rate of about 30 lpm. Significantly, it has been shown that in a valve body having an L/D' ratio of about 0.6, the pressure drop through the valve at a flow rate of about 30 lpm is reduced by about 28 percent, as compared to a similar valve having an L/D' ratio of about 0.3. This alone is an extremely significant improvement in prosthetic valve operating characteristics which is of even more importance at higher flow rates where the reduction in pressure drop is even more striking. However, there are also other features of significantly improved hemodynamic performance that ensue from the use of such a bi-leaflet valve. Lower pressure drops not only mean that less work must be done by the heart, but almost as importantly, lower pressure drops mean lower blood velocities and shear stresses, which translate to reduced blood damage—a significant additional benefit.

Although the invention has been described with respect to a number of preferred embodiments, which include the best mode believed by the inventors to create such advantages in improved flow through an open bi-leaflet valve, it should be understood that various changes and modifications as would be obvious to one having the ordinary skill in this art may be made without departing from the scope of the invention which is defined by the claims appended hereto.

Particular features of the invention are emphasized in the claims that follow.

What is claimed is:

1. A bi-leaflet prosthetic heart valve which comprises a generally annular valve body having an interior sidewall which defines a generally cylindrical central passageway therethrough for the passage of blood in a downstream direction, said passageway having a longitudinal axis extending in the direction of blood flow and being circular in cross section except for a pair of diametrically opposed flat interior sidewall surfaces, said cylindrical sidewall surfaces being smooth, straight and parallel to said longitudinal axis, said valve body having means for mounting within a human heart, a pair of leaflets, each having a flat inflow surface and a flat outflow surface and being of substantially uniform thickness except for regions along both opposite lateral edges wherein elements forming a part of a pivot arrangement are located, said leaflets being mounted in said valve body by said pivot arrangement to open and close together to alternately permit the flow of blood therethrough past both said surfaces of each leaflet in a downstream direction when in the open position and block the flow of blood in the reverse direction when in the closed position, said valve body and said leaflets being interconnected by said pivot arrangement so that said leaflets are guided in movement between said open positions and said closed positions, said pivot arrangement being located along the regions of said flat sidewall surfaces in said valve body, said leaflets and said pivot arrangement being constructed so that, when said leaflets are in said open position, both said flat outflow surfaces and said flat inflow surfaces thereof can assume an alignment parallel to said longitudinal axis, with said leaflets each being spaced from said axis by a distance not greater than about one-half the radius of said circular passageway, said spacing being such as to create regions of very substantially blood flow adjacent both said inflow and outflow surfaces of both leaflets, said pivot arrangement being such that from said open position said leaflets translate immediately upstream and pivoting movement toward said closed position is positively initiated during each translation as a result of contact between each said leaflet and said valve body which applies a camming force to each said leaflet, the cross sectional area of said central passageway being equal to the area of a circle with diameter D', and said valve body being axially elongated so that its minimum axial length is such that the ratio of said minimum length to said diameter D' of said central passageway is at least about 0.5:1 and not greater than about 1.2:1, whereby normal blood flow through said valve passageway in the open position is of a streamlined nature, with low turbulence and pressure drop through said heart valve.

2. A prosthetic heart valve according to claim 1 wherein the diameter D' is at least equal to about 95% of the diameter of said passageway measured parallel to said flat sidewall surfaces.

3. A prosthetic heart valve according to claim 2 wherein said valve body has a curved entrance edge and a curved exit edge leading toward and away from said interior parallel sidewall section.

4. A prosthetic heart valve according to claim 1 wherein said ratio is between about 0.6:1 and about 1:1.

* * * * *

UNITED STATES PATENT AND TRADEMARK OFFICE
CERTIFICATE OF CORRECTION

PATENT NO. : 5,137,532
DATED : August 11, 1992
INVENTOR(S) : Bokros et al

It is certified that error appears in the above-indentified patent and that said Letters Patent is hereby corrected as shown below:

Column 12, line 18, change "substantially" to --substantial--.

Signed and Sealed this

Twenty-fifth Day of October, 1994

Attest:

BRUCE LEHMAN

*Attesting Officer*  *Commissioner of Patents and Trademarks*